«12» United States Patent
Hohensinner et al.

«10» Patent No.: US 8,061,240 B2
«45» Date of Patent: Nov. 22, 2011

«54» METHOD AND DEVICE FOR STRIPPING OR TRIMMING SAMPLES TO BE EXAMINED RHEOLOGICALLY

«75» Inventors: Heinz Hohensinner, Gössendorf (AT); Michael Krenn, Zettling (AT)

«73» Assignee: Anton Paar GmbH, Graz-Strassgang (AT)

«*» Notice: Subject to any disclaimer, the term of this patent is extended or adjusted under 35 U.S.C. 154(b) by 372 days.

«21» Appl. No.: 12/432,781

«22» Filed: Apr. 30, 2009

«65» Prior Publication Data

US 2009/0272178 A1   Nov. 5, 2009

«30» Foreign Application Priority Data

Apr. 30, 2008   (AT) .................................. A 686/2008

«51» Int. Cl.
*B26F 1/00*   (2006.01)
*B23B 3/00*   (2006.01)
«52» U.S. Cl. ........................................................ 82/1.11
«58» Field of Classification Search ................... 82/1.11, 82/46, 47, 51, 117, 118; 73/54.37, 54.28; 83/919
See application file for complete search history.

«56» References Cited

U.S. PATENT DOCUMENTS

| | | | | | |
|---|---|---|---|---|---|
| 2,780,096 | A | * | 2/1957 | Noble et al. | 73/150 R |
| 4,449,395 | A | * | 5/1984 | Kurtz et al. | 73/54.11 |
| 4,664,004 | A | * | 5/1987 | Randall | 83/125 |
| 5,522,719 | A | * | 6/1996 | Umeda et al. | 425/380 |
| 7,275,419 | B2 | | 10/2007 | Raffer | |
| 2002/0078768 | A1 | * | 6/2002 | Hiatt et al. | 73/864.41 |

FOREIGN PATENT DOCUMENTS

DE   102005001437 A1   12/2005

* cited by examiner

*Primary Examiner* — Will Fridie, Jr.
«74» *Attorney, Agent, or Firm* — Laurence A. Greenberg; Werner H. Stemer; Ralph E. Locher

«57» ABSTRACT

A method and device allow automatic trimming of samples for the measurement of the rheological properties of material samples by way of a plate/plate rheometer. In order to strip the protruding portion of the material sample arranged between the plates that projects over the circular circumferential edges of the rheometer plates—a cutting edge, which at its setting angle with respect to the tangent is pressed against the circular circumferential edge of the plates at the line of contact and pertains to the blade of the stripping tool that is stayed, in particular articulated, by means of a holding strut at a holding point of a holding block, and the plates of the rheometer —relative to each other—are moved in rotation in a circle with respect to each other in at least a fully circumferential circular rotational movement, wherein the circular rotational movement is guided in such a way that the real or virtual relative rotational advance of the cutting edge of the stripping-tool blade is effected counter to the virtual or real circumferential circular rotational advance respectively of the rheometer plates.

20 Claims, 3 Drawing Sheets

METHOD AND DEVICE FOR STRIPPING OR TRIMMING SAMPLES TO BE EXAMINED RHEOLOGICALLY

CROSS-REFERENCE TO RELATED APPLICATION

This application claims the priority, under 35 U.S.C. §119, of Austrian patent application A 686/2008, filed Apr. 30, 2008; the prior application is herewith incorporated by reference in its entirety.

BACKGROUND OF THE INVENTION

Field of the Invention

The present invention relates to a method for automatically stripping or trimming samples in the course of a reproducible measurement of the rheological properties of highly viscous and solid samples, such as asphalt or polymer samples for example, in a plate/plate rheometer.

The relative circular rotational movement provided in accordance with the claims is guided in such a way that the real and/or virtual relative rotational advance of the cutting edge of the stripping-cutter blade is effected counter to the virtual and/or real circumferential circular rotational advance of the plates (1,1'). The expressions "virtual" and "real" rotational advance denote the two variants of the relative movement: either the cutter is moved around the two measuring portions of the rheometer or the two measuring portions are moved synchronously along the stationary cutter by rotating the two measuring portions about the common axis.

A new device for carrying out the new method constitutes further important subject matter of the invention.

Rotation rheometers, as described, for example, in the commonly assigned U.S. Pat. No. 7,275,419 B2 and German published patent application DE 10 2005 001 437 A1 can be equipped with very different measuring bodies. These are standardized in part and substantially comprise cone/plate, plate/plate and cylinder measuring systems.

The plate/plate measuring system comprises two planar, circularly round plates. As a rule, the upper plate forms the rotationally movable part of the measuring geometry and is mounted on a measuring shaft with a measuring motor (rotor), whilst the lower fixed plate (stator) is secured on the rheometer stand at a defined distance. With this geometry, the rheometer opens up the possibility of different rheological examinations.

In addition to so-called CSR tests, where a constant speed is applied to the measuring shaft and the torque is measured, and CSS tests, where a constant torque is applied and the speed or the rotational position is measured, oscillation tests are also possible by applying a rotational movement in wave form to the measuring shaft.

The two sequences of letters CSR and CSS mentioned above have the following meaning: CSR is the abbreviation for Controlled Shear Rate and stands for carrying out tests with predetermination of the shear rate, and CSS is the abbreviation for Controlled Shear Stress and signifies carrying out tests with the rotational rheometer with predetermination of shear stress.

CSR is usually chosen when the sample fluid runs by itself and the viscosity is to be simulated at defined flow rates, whilst the CSS test is the classic method for flow-limit determination of dispersions, pastes or gels.

The rheometer just described predetermines the movement of the one plate portion given simultaneous measurement of the torque acting on the same plate. Measuring arrangements that differ therefrom with separation of the driving motor for the rotation and measurement of the torque with similar plate/plate geometry are known and can be equipped with the stripping or trimming tool in accordance with the invention without any problem.

In comparison with rheological measurements with other geometries, in accordance with the known Couette principle with cylinder geometry for example, the plate/plate measuring systems present the advantage that samples with a three-dimensional structure, hardening and cross-linking substances to soft solid bodies in disc form can also be examined rheologically therewith.

Examples of application therefor are pastes, molten masses of filled polymers, granular bodies or pellets, elastomers, rubber, compressed powders, asphalt and the like. Details of such tests can be found, for example, in "Das Rheologie Handbuch", 2nd edition, by Thomas Metzger, Vincentz Network/Coatings Compendia, Hanover, (2006).

Many of the samples that are of interest in connection with their rheology demonstrate time- and/or temperature-dependent behavior. At low temperatures below the melting temperature, complex superstructures can be present in a rigid form like a solid body; the samples are inflexible and brittle. During heating, they then soften and have a flow property.

An important application for this special case is, for example, the measurement of polymer samples and also of asphalt or bitumen, that is, of typically thermoviscous substances, whose behavior usually changes continuously with the temperature. The requirements for road-building bitumen are laid down in EN 12 591, for example.

It is known that in examinations on viscoelastic substances in rheometers with plate/plate geometry, edge effects occur, such as, for example, gap-emptying or creepage out of the gap between the plates, that falsify the measurement result in each case as a function of the measuring geometry. The determining influence of edge effects has been known for a long time and has led to different recommendations; for example ISO 6721-10 prescribes defined values for polymer checks for the ratio of the plate diameter (2R) to the height of the measurement gap (H) between the plates.

In addition, in order to determine the rheological properties of asphalt precise measurement prescriptions exist for sample-preparation (e.g. ASTM D7175-07/AASHTO T315-06). The standard measuring method describes the preparation for measuring asphalt pellets in a plurality of steps. The small sample piece is laid onto the lower, usually fixed plate and pre-tempered. After reaching the respectively predetermined starting temperature, the upper plate is lowered so far that the upper sample side and the lower plate side of the measuring plate just touch. Afterwards, the portion of the sample that may possibly have swollen out or protrude over the edge of the plates has, up until now, been removed by stripping the protruding portion along the plate edge by hand.

Subsequently, by means of a small advance of the upper plate or by reducing the distance between the plates by 50 µm the sample is slightly pre-tensioned between the plates. Thus for each test approximately the same bulgy sample geometry is available between the plates with sufficient adhesion of the sample on the plate faces in order to determine the rheological characteristic variables of the same.

Similar procedures are also selected when preparing other solid-body samples, in particular in the case of pellet samples of highly viscous or solid material.

The fixed plate is adjusted in the center in order to receive the sample. The upper plate known per se is, as described, lowered onto the sample and in this way contact is established between sample surfaces and inner plate faces.

Afterwards, the protruding sample is stripped by hand by means of cutters, wire, scrapers or the like at a certain angle at the plate edge. If applicable, the distance between the two plates before and/or after the stripping is reduced by a defined amount of advance.

The lack of reproducibility of this process represents quite a substantial disadvantage of stripping the portions of sample that protrude at the edge by hand. The temperature of the stripping tool, the setting angle of the stripper against the sample surface and the type of processing, that is, in particular the pressure that is exerted on plate edges during stripping or else whether there is circumferential travel in one continuous working operation or with repeated stopping, lead to differing edge geometries which, as known, influence the measurement result.

In many test surveys, such as, for example, in quality-monitoring in production processes, in the development of additives for polymer samples and the like, the comparability of the individual measurements and the determination of the changes in the rheological parameters of the respective samples are of essential importance.

SUMMARY OF THE INVENTION

It is accordingly an object of the invention to provide a method of stripping or trimming samples for rheologic examination which overcomes the above-mentioned disadvantages of the heretofore-known devices and methods of this general type and which renders possible for the first time trimming of highly viscous samples in a plate/plate rheometer in a manner which is actually reproducible, in order to achieve a substantial improvement in the reproducibility and comparability of the individual measurements.

With the foregoing and other objects in view there is provided, in accordance with the invention, a method of automatically stripping or trimming samples for a reproducible measurement of the rheological properties of highly viscous to solid material samples by way of a plate/plate rheometer prior to carrying out the measurement, the method which comprises:

clamping a material sample between two plates of the rheometer, the plates having a circular circumferential edge;

providing a stripping tool with a cutting blade supported by way of a holding strut on a holding block;

placing a cutting edge of the cutting blade with a setting angle relative to a tangent against the circular circumferential edge of the plates to form a line of contact; and moving the plates of the rheometer and the cutting of the cutting blade relative to one another in rotation in a circle with respect to one another in at least one full circumferential circular rotational movement in order to strip a protruding portion of the sample material projecting over the circular circumferential edge of the plates of the rheometer.

The substantial advantage of the new method lies in the fact that the edge effects, which have been explained above and unfavorably influence or even falsify the reproducibility, as a consequence of irregularly stripped protruding portions of sample or irregular sample edges, are minimized or practically eliminated in the measuring system.

A further advantage of the new arrangement operating in accordance with the new method for trimming the sample consists in the ability to automate the measurements.

If, for example, there is a desire to use a high-throughput rheometer, such as, for example, one such rheometer that is produced by the applicant with an automatic sample-changer for high sample throughput by means of Anton Paar RoboticRheometry™ measuring robots, for pellet samples that are to be trimmed as well, the trimming of the samples should or must also be effected by means of an automatically operating device for stripping the protruding portion of sample. This device, as mentioned briefly at the beginning, constitutes further important subject matter of the invention.

It will be understood, in the context of the invention, that it is important to ensure that there is a difference between the rate of rotational advance of the circumferential edge of the plates of the rheometer holding the material sample between them and the rate of rotational advance of the cutting edge of the blade of the stripping tool, in which case the relative rotational advance of the plate edges must be effected in the direction of the blade or its cutting edge.

According to an example of the invention, there is provided detailed information about the angle which is to be observed in an advantageous way between the blade of the stripping tool and the circumferential edge of the rheometer plates at the point or line of contact of the stripping cutting edge at the circumferential edge of the plates. In this case, the blade of the stripping cutter or its cutting edge along its line of contact with the tangent at the circular circumferential plate edge along the line of contact of the plates adopts an angle of 1 to 45°, in particular of 5 to 25°.

In accordance with an added feature of the invention, the blade of the stripping cutter or its cutting edge that is held so that it rests or is pressed against the circular circumferential edge of the plates is moved in rotation in a circle about the fixed plates of the rheometer at least for one full circling. That is, there is presented a way of carrying out the new stripping method which is particularly advantageous within the scope of the invention with fixed rheometer plates and the cutting edge or blade of the new stripping tool that is guided in a circle around the latter and ensures that the removal of the protruding portion of sample material is effected in a reproducible manner.

As already mentioned above, a new device for carrying out the new method, preferably in accordance with claim 4, constitutes further important subject matter of the present invention.

With the above and other objects in view there is also provide, in accordance with the invention, a device for automatically stripping or trimming samples for a subsequent reproducible measurement of the rheological properties of highly viscous to solid material samples by way of a plate/plate rheometer, the device being configured to perform the above-outlined method. The device according to the invention comprises:

a table secured to the plate/plate rheometer with a stripping-tool-holding ring configured to be set into a concentric circular rotational movement about the plates of the rheometer by way of a driving motor and a driving wheel substantially without contacting the plates or the circumferential edges thereof, whereby the plates hold the material sample to be examined therebetween;

a holding block with a stripping tool held by said block mounted on said holding ring and rotatable therewith, and wherein said stripping tool is subjectible to a force acting to force said stripping tool towards the plates for a predetermined number of fully circumferential circular rotations which, optionally are interrupted or wave-like, and which can then be folded away laterally;

said stripping tool having a lever with a free end and a blade secured to said free end, said blade having a cutting edge on a front side thereof to be held resting on, or pressed against, a circumferential edge of the plates at a given setting angle with respect to the circumferential edge.

Preferably, the stripping-tool-holding ring has on its outer periphery a toothed wheel rim which meshes with a toothed wheel forming the motor-driven holding-ring-driving wheel. Or, in the alternative, the holding-ring driving wheel is rotationally connected to the stripping-tool-holding ring by means of belts, V-belts or link chain. That is, there are provided two different exemplary embodiments of the rotary drive for the stripping-tool-holding ring.

A special form of the toothed-wheel drive may be provided, as follows: The stripping-tool-holding ring is provided with a fully circumferential circulating furrow or groove into which there engage at least three holding wheels which are mounted so that they are spaced apart from each other on the holding table, have circumferential edges having a counter-cross-sectional form substantially corresponding to the cross-sectional form of the furrow mentioned, and are provided for the holding support and rotational guidance of the stripping-tool-holding ring, which without an axle shaft can be moved in rotation in a circle concentrically about the rheometer plates.

It is advantageous to provide for the blade of the stripping tool and thus its cutting edge to be heated, in particular by means of electrical resistance heating, induction heating or a Peltier element, to a respective temperature predetermined as a function of the sample material.

In accordance with another feature of the invention, the blade of the stripping tool is formed from a heat-resistant and sample-material-resistant material, in particular metal, preferably steel, from a hard metal, from ceramic material or hard ceramic material or from pure plastics material.

In accordance with a concomitant feature of the invention, the there is provided an arrangement, secured on the holding table and fitted or formed preferably with a hydraulic or pneumatic cylinder or with an electric or pneumatic switch, for applying, with the possibility of action of force or with the action of force, if applicable in an adjustable manner, the cutting edge of the blade of the stripping tool against the circumferential edge of the plates or for folding away the same from the circumferential edge mentioned after in each case a predetermined number of revolutions. This provides detailed exemplary information about the arrangement for applying the tool blade to the circumferential edge of the rheometer plates for stripping the protruding portion of sample and for swinging the blade away after the respectively predetermined number of stripping revolutions have been run through.

Other features which are considered as characteristic for the invention are set forth in the appended claims.

Although the invention is illustrated and described herein as embodied in a method for stripping or trimming samples that are to be examined rheologically, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
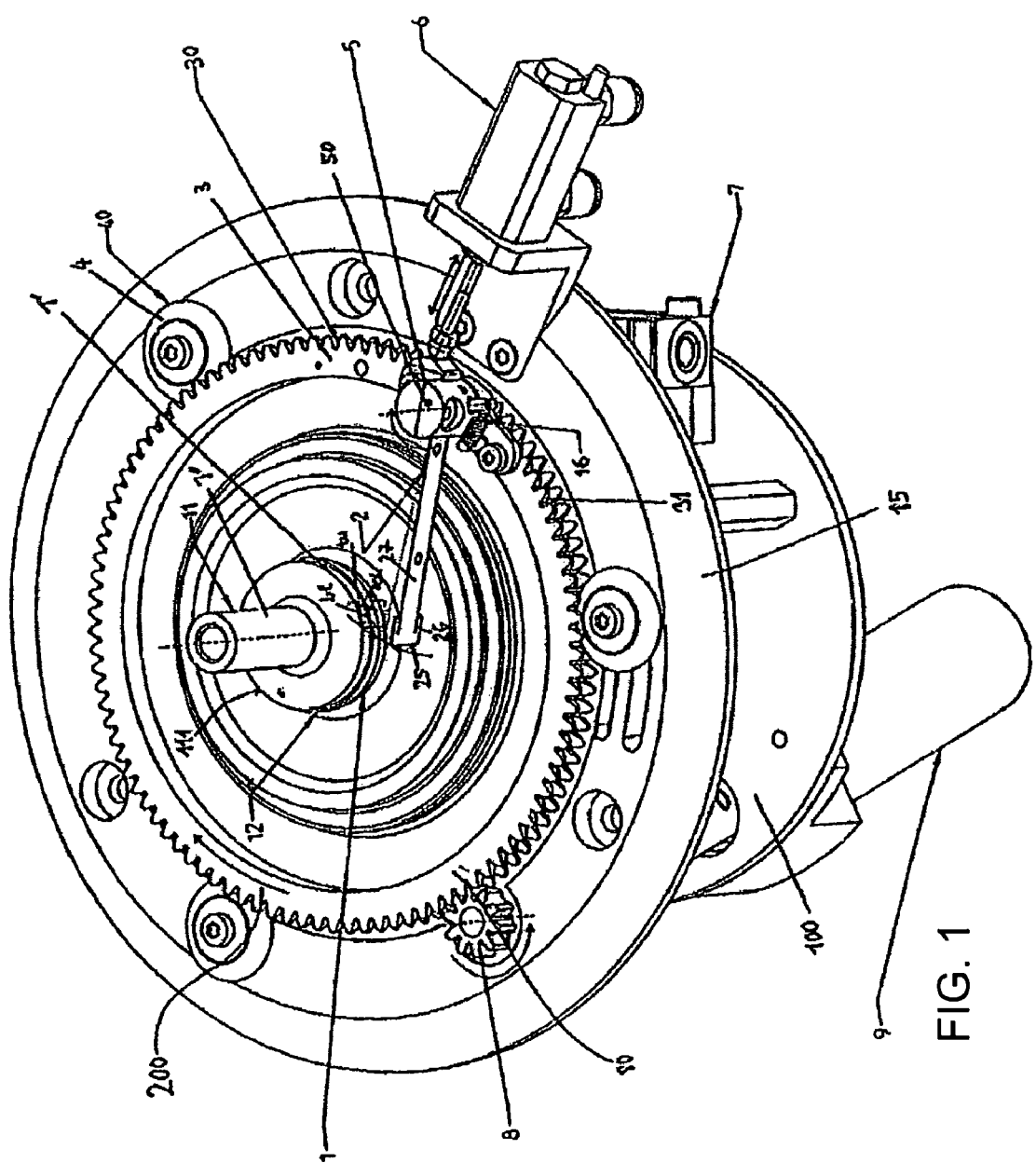
FIG. 1 is a perspective view of a preferred embodiment of the automatic trimming device for a rotation rheometer (cf. U.S. Pat. No. 7,275,419 B2 and DE 102005001437 A1)

Referring now to the figures of the drawing in detail, there is shown a new automatic trimming device 200 in a preferred embodiment for a rotation rheometer 100; the method in accordance with the invention will be explained in the context of the devices 200 and 100.

A circularly round plate 1 forms a fixed lower measuring plate and numeral 12 designates an inserted pellet of a sample which, for example, is highly viscous. Numeral 11 denotes the system of an upper rotatable plate 1' and a measuring shaft 1" of the latter's motor of a known plate/plate rheometer 100.

The lower portion of the rheometer 100 is now formed in departure from the prior art embodiment. In addition to the holding support for the lower plate 1 it has a table 15 that encircles the rheometer here on all sides and on which by means of a rotational advancing device 80 a stripping tool 2 with a distal blade 26 with a cutting edge 25 on the front side is moved in a circular circulating rotational movement around the plates 1, 1' of the rheometer 100.

The rotational advancing device 80 is realized here by means of a stripping-tool-holding ring 3, which has a toothed rim 30 on the outside, and a driving motor 9 with a driving toothed wheel 8 that is driven by the latter and meshes with the toothed rim 30 just mentioned. The toothed rim 30 of the holding ring 3 is here constructed with a rotational guiding groove of furrow 31 deeper in the latter's teeth, preferably in the center, and in cooperation with position-holding elements, here three rotational guiding wheels 4 with a periphery 40 having a form that corresponds to the form of the rotational guiding groove 31, they mount and rotationally guide the stripping-tool-holding ring 3 in a free three-point bearing on or above the table 15.

Any useful alternative in the sense described, such as an embodiment, for example, with a driving groove in or on the table and drive by means of a snap ring or the like, or drive by means of a V-belt, chain and a plurality of support points, support wheels or the like, can be used. Of course, the drive can also be effected by means of a pneumatic motor instead of by means of an electric motor.

Furthermore, it is basically unimportant whether the stripping tool 2 with its holding and pressing block 5 in accordance with FIG. 1 is guided in a circle around the stationary plate/plate measuring arrangement of the rheometer 100 or whether the two plates 1, 1' move in rotation past the stripping blade 26 of the stationary stripping tool 2 or its cutting edge 25.

In this connection, the lower plate 1 can be synchronously moved in rotation by means of the controllable driving motor together with the sample to be tested for its rheological properties and resting on the plate, or the pellet resting thereon, in synchronism together with the upper plate 1' resting thereon, whilst the stripping tool 2 or its blade 26 is fixed.

The actual stripping element that strips the protruding portion of sample is preferably the cutting edge 25 of a blade 26 that can be applied to or is applied to the circular circumferential edge 111 of the plates 1, 1' along the line of contact bl and is of any form and made from metal or any other material, such as ceramic material or plastics material for example, in which case there must be chemical resistance with respect to the material that is to be stripped and sufficient thermal resistance with adequate thermal conductivity.

Advantageously, the blade 25 of the stripping tool 2 or the whole tool 2 is easy to exchange and clean. In the form presented here, it or its arm 27 is held fast by means of a holding support that can be released simply, preferably by means of a spherical holding support in the holding block 5; in the automated form, the cutter or the blade 26 can, if applicable, be removed by vacuum suction apparatus and be replaced by means of a robotic arm.

For this purpose, a folding action out or away from the plate edge 1 can be effected by means of a pulse transmitter 6, preferably a compressed-air switch, a hydraulic or pneumatic cylinder, that acts at the edge of the rotatably or swivel-mounted holding block 5 and by means of rotation or a swing away of the holding block 5 lifts the stripping tool 2 off from the sample 12 or from the circular circumference of the plates 1, 1' in opposition to the direction of swing symbolized by an arrow in FIG. 1.

In the folded-to state, that is, in the state resting against the circumferential edge 111 of the plates 1, 1', the stripping tool 2 or its blade 26 or its cutting edge 25 is pressed in an elastically pre-tensioned manner against the circumferential plate edge 111 or the circumferential sample edge defined by the same. This can be effected, for example, by means of a spring element, such as, for example, by means of a spiral spring 16 that can be seen in FIGS. 1 and 2. The thus pre-tensioned blade 26 or its cutting edge 25 is used to lift off in a uniform manner the material of the sample 12 to be tested that protrudes over the circumferential plate edge 111. The angle α between the blade 26 at the line of contact b1 of the cutting edge 25 with the edge 111 and the tangent tu at the circumferential edge 111 of the plates 1, 1' here amounts to, for example, approximately 10°.

Figure 2:
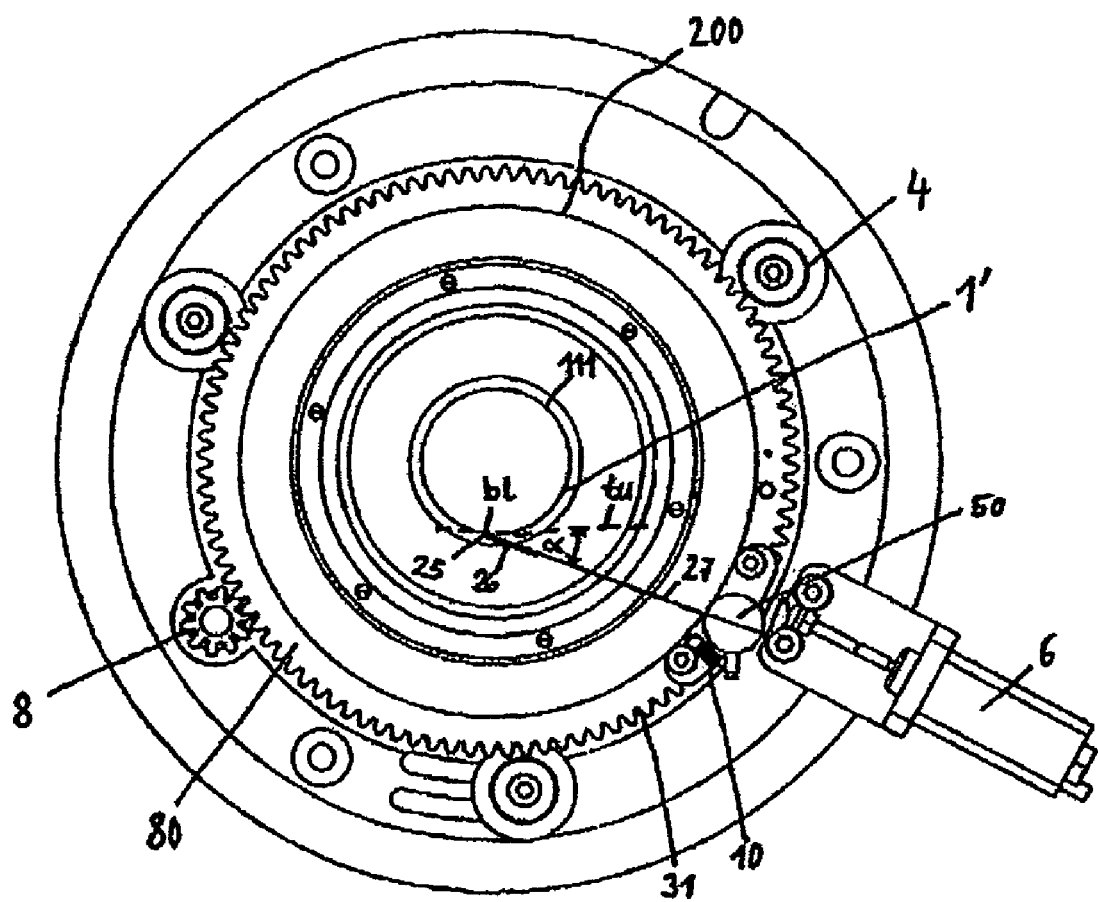
FIG. 2 is a plan view thereof.
Figure 3:
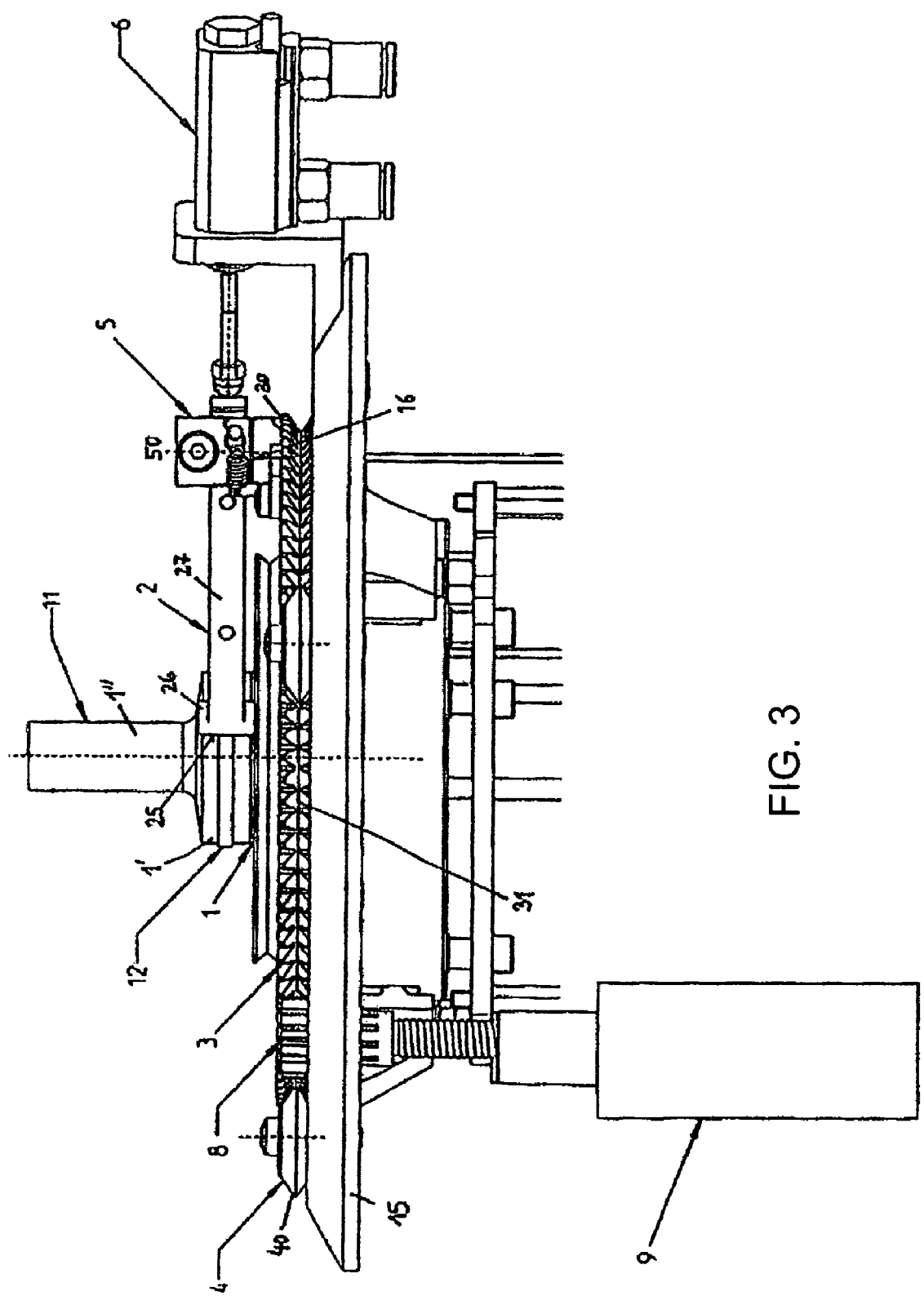
FIG. 3 is a side view thereof.

The angle α between the cutting-edge course and the tangent tu at the line of contact b1 of the cutting edge 25 of the blade 26 with the circumferential edge 111 can be seen clearly in FIG. 2—where otherwise the significance of the reference symbols remains the same.

In this connection, both the sample 12 and/or the stripping tool 2 or its blade 26 with cutting edge 25 can be pre-tempered to a respective temperature that is favorable for stripping, for example by means of a separate heating device for the stripping tool 2 or its blade 26, or else preferably by heating the sample or the sample material 12, for example by means of the Peltier chamber known from AT 409422.

The counter-rotating relative rotational movement of the sample 12 that is arranged between the plates 1, 1' and projects over their circumferential edge 111 and the blade 26 or its cutting edge 25 respectively is advantageously monitored by means of a preferably visual signal transmitter 7; this monitoring can, however, also be effected inductively, capacitively or magnetically.

The driving motor 9 or the rotational advance of the tool-holding ring 3 produced by it in relation to the plates 1, 1' is controlled preferably in a feedback loop and it is further ensured that a respectively predetermined number of revolutions or rounds of stripping is effected. The application or adaptation of the cutting edge 25 of the blade 26 to the circumferential edge 111 of the plates 1, 1' or the folding away of the same from there is effected by means of the tool-actuating device 6, which is preferably controlled by the sensor 7.

The respective parameters are advantageously processed and stored in an electronic control unit of the rheometer 100, which is not further represented, and, if the control of the rotational advancing motor 9 is also effected for the driving toothed wheel 8 on the basis of the signals of the signal transmitter 7, the rate of rotational advance can also be regulated, and adapted to the respective material of the sample 12 that is to be trimmed, in the zone of the initial rotation or start of trimming, during the trimming and when the blade 26 is lifted off from the circumferential edge 111 of the plates 1, 1'.

The protruding material of the sample 12 that has been removed by means of the new stripping tool falls downwards in the simplest case and is collected, for example in a catching device, thereby preventing contamination of the equipment as a whole.

The invention claimed is:

1. A method of automatically stripping or trimming samples for a reproducible measurement of the rheological properties of highly viscous to solid material samples by way of a plate/plate rheometer prior to carrying out the measurement, the method which comprises:
    clamping a material sample between two plates of the rheometer, the plates having a circular circumferential edge;
    providing a stripping tool with a cutting blade supported by way of a holding strut on a holding block;
    placing a cutting edge of the cutting blade with a setting angle relative to a tangent against the circular circumferential edge of the plates to form a line of contact; and
    moving the plates of the rheometer and the cutting of the cutting blade relative to one another in rotation in a circle with respect to one another in at least one full circumferential circular rotational movement in order to strip a protruding portion of the sample material projecting over the circular circumferential edge of the plates of the rheometer.

2. The method according to claim 1, wherein the material sample is clamped between the plates with a defined, variable clamping.

3. The method according to claim 1, wherein the holding strut is articulated on the holding block at a holding point defining a point of articulation.

4. The method according to claim 1, which comprises pressing the cutting blade against the circular circumferential edge with adjustable pressure.

5. The method according to claim 1, which comprises setting the blade of the stripping cutter with a cutting edge along a line of contact with the tangent at the circular circumferential plate edge along the line of contact of the plates to adopt an angle of 1 to 45°.

6. The method according to claim 5, which comprises setting the angle to between 5 and 25°.

7. The method according to claim 1, which comprises moving the blade of the stripping cutter, resting on or pressed against the circular circumferential edge of the plates, in rotation in a circle about the fixed plates of the rheometer at least for one full circling.

8. A device for automatically stripping or trimming samples for a subsequent reproducible measurement of the rheological properties of highly viscous to solid material samples by way of a plate/plate rheometer, the device being configured to perform the method according to claim 1 and comprising:
    a table secured to the plate/plate rheometer with a stripping-tool-holding ring configured to be set into a concentric circular rotational movement about the plates of the rheometer by way of a driving motor and a driving wheel substantially without contacting the plates or the circumferential edges thereof, whereby the plates hold the material sample to be examined therebetween;
    a holding block with a stripping tool held by said block mounted on said holding ring and rotatable therewith, and wherein said stripping tool is subjectible to a force acting to force said stripping tool towards the plates for a predetermined number of fully circumferential circular rotations which, optionally are interrupted or wave-like, and which can then be folded away laterally;

said stripping tool having a lever with a free end and a blade secured to said free end, said blade having a cutting edge on a front side thereof to be held resting on, or pressed against, a circumferential edge of the plates at a given setting angle with respect to the circumferential edge.

9. The device according to claim 8, wherein said table substantially encircles the plate/plate rheometer.

10. The device according to claim 8, wherein said stripping tool is swivel-mounted on said holding block and wherein a spring biases said stripping tool towards the plates.

11. The device according to claim 8, wherein said cutting blade is detachably mounted to said free end.

12. The device according to claim 8, wherein said stripping-tool-holding ring has an outer periphery formed with a toothed wheel rim disposed to mesh with a toothed wheel forming a motor-driven holding-ring-driving wheel.

13. The device according to claim 8, wherein said holding-ring driving wheel is rotationally connected to said stripping-tool-holding ring by way of a connector selected from the group consisting of a belts, a V-belts. and a link chain.

14. The device according to claim 8, wherein said stripping-tool-holding ring is formed with a fully circumferential circulating groove into which there engage at least three holding wheels mounted spaced apart from one another on said holding table, said holding wheels having circumferential edges with a counter-cross-sectional form substantially corresponding to a cross-sectional form of said groove, and provided for a holding support and rotational guidance of said stripping-tool-holding ring, which without an axle shaft can be moved in rotation in a circle concentrically about the plates of the rheometer.

15. The device according to claim 8, wherein said blade of said stripping tool and said cutting edge thereof can be heated to a temperature predetermined in dependence on a material of the sample.

16. The device according to claim 15, which comprises a heating device selected from the group consisting of an electrical resistance heater, an induction heater, and a Peltier element for heating said blade.

17. The device according to claim 8, wherein said blade of said stripping tool is formed of a heat-resistant and sample-material-resistant material.

18. The device according to claim 8, wherein said material of said blade is selected from the group consisting of metal, ceramic material, hard ceramic material, or pure plastics material.

19. The device according to claim 18, wherein said material is steel.

20. The device according to claim 8, which comprises an arrangement secured on said holding table, optionally fitted or formed with a hydraulic or pneumatic cylinder or with an electric or pneumatic switch, for forcing said cutting edge of said blade of the stripping tool against the circumferential edge of the plates or for folding away said blade from the circumferential edge in each case a predetermined number of revolutions.

\* \* \* \* \*